United States Patent
Miyoshi et al.

(10) Patent No.: US 7,189,220 B2
(45) Date of Patent: Mar. 13, 2007

(54) DIAPER FASTENER WITH TWO NONWOVEN FABRIC COMPONENTS COATED WITH THERMOPLASTIC SYNTHETIC RESIN

(75) Inventors: Takayuki Miyoshi, Kagawa-ken (JP); Hisashi Takai, Kagawa-ken (JP); Hironao Minato, Kagawa-ken (JP); Koichiro Mitsui, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/910,368

(22) Filed: Aug. 4, 2004

(65) Prior Publication Data
US 2005/0033257 A1     Feb. 10, 2005

(30) Foreign Application Priority Data
Aug. 5, 2003    (JP) ............................... 2003-205918

(51) Int. Cl.
*A61F 13/58*    (2006.01)
*A61F 13/62*    (2006.01)

(52) U.S. Cl. ................. 604/389; 604/391; 428/130; 428/40.1; 428/343

(58) Field of Classification Search ........ 604/387–389, 604/366–367, 370–372, 385.03; 156/327; 162/157.2; 428/355; 252/62.54; 24/451
See application file for complete search history.

(56) References Cited

U.S. PATENT DOCUMENTS

| | | | | |
|---|---|---|---|---|
| 4,710,190 A | * | 12/1987 | Wood et al. | ................. 604/389 |
| 4,787,897 A | * | 11/1988 | Torimae et al. | ............. 604/389 |
| 5,019,071 A | * | 5/1991 | Bany et al. | ................. 604/389 |
| 5,106,383 A | * | 4/1992 | Mulder et al. | .............. 604/389 |
| 5,182,156 A | * | 1/1993 | Pape et al. | ................... 428/130 |
| 5,738,930 A | * | 4/1998 | Huskey | ...................... 428/156 |
| 6,129,964 A | * | 10/2000 | Seth | ........................... 428/40.1 |
| 2001/0039409 A1 | * | 11/2001 | Minato et al. | ......... 604/385.28 |
| 2003/0219591 A1 | * | 11/2003 | Bany et al. | ................. 428/343 |

FOREIGN PATENT DOCUMENTS

| | | | |
|---|---|---|---|
| EP | 0487758 A1 | * | 6/1992 |
| EP | 0893114 A2 | * | 1/1999 |
| JP | 1997-38139 | | 2/1997 |

* cited by examiner

*Primary Examiner*—Tatyana Zalukaeva
*Assistant Examiner*—Laura C Hill
(74) *Attorney, Agent, or Firm*—Lowe Hauptman & Berner LLP (57) ABSTRACT

A disposable diaper includes a pair of tape fasteners 6 that are used to connect front and rear waist regions 8, 10 to each other and are attached to side flaps 14 in the rear waist region 10 of the diaper. Each of the tape fasteners 6 includes fibrous nonwoven fabric made of thermoplastic synthetic resin fiber and thermoplastic synthetic resin coated on a substantially whole area of an outer surface of the fibrous nonwoven fabric wherein the thermoplastic synthetic resin forms a substantially smooth synthetic resin layer on outer surfaces of the respective tape fasteners. Thus, a free portion of each tape fastener is reliably prevented from being disengaged from a target tape even when the outer surface of the tape fastener and an inner surface of an underwear rub together during use of the diaper.

24 Claims, 9 Drawing Sheets

DIAPER FASTENER WITH TWO NONWOVEN FABRIC COMPONENTS COATED WITH THERMOPLASTIC SYNTHETIC RESIN

RELATED APPLICATIONS

The present application is based on, and claims priority from, Japanese Application Number 2003-205918, filed Aug. 5, 2003, the disclosure of which is hereby incorporated by reference herein in its entirety.

BACKGROUND OF THE INVENTION

The present invention relates to a disposable diaper for absorption and containment bodily discharges.

There has already been proposed an open-type disposable diaper defining, in a longitudinal direction, front and rear waist regions and a crotch region extending between these two waist regions, wherein a pair of tape fasteners extending in a transverse direction and used to connect the front and rear waist regions with each other are attached to side flaps of the rear waist region, respectively, and a target tape is attached to the front waist region so that the tape fasteners may be releasably anchored on the target tape (See Japanese Unexamined Patent Application Publication No. 1997-38139, hereinafter referred to as "Citation").

The tape fasteners are formed from a fibrous nonwoven fabric made of a plurality of thermoplastic synthetic resin fibers entangled one with another. The tape fasteners respectively have fixed portions adapted to be permanently bonded to respective transversely outer ends of the side flaps in the rear waist region and free portions extending outward from the respective fixed portions in the transverse direction. The free portions of the respective tape fasteners are provided on respective inner surf aces thereof with hooks constituting a mechanical fastener. The target tape is provided in the form of a rectangular strip being relatively long in the transverse direction and formed from a bulky nonwoven fabric made of a plurality of thermoplastic synthetic resin fibers entangled one with another. To put the diaper disclosed in Citation on the wearer's body, the side flaps of the rear waist region are placed upon the outer side of the front waist region and then the free portions of the tape fasteners are anchored on the target tape through the intermediary of the hooks to connect the front and rear waist regions with each other. Parent or care personnel puts underwear such as pants or skirt on the wearer having the diaper thereon. Movement of the wearer's body having the diaper put thereon causes the outer surface of the tape fastener and the inner surface of the underwear to rub together.

In the diaper disclosed in Citation, the tape fasteners are formed from the fibrous nonwoven fabric made of a plurality of thermoplastic synthetic resin fibers and the outer surface of each tape fastener is not smooth but relatively rough. Therefore, a certain sliding friction is exerted upon the tape fastener by the underwear as the outer surface of the tape fastener and the inner surface of the underwear rub together. Such sliding friction may cause torsion and/or turning up of the free portion of the tape fastener. In this diaper, the torsion and/or turning up of the free portion of the tape fastener nay be exerted upon the tape fastener and the target tape as shearing force and/or peel force intending to disengage the tape fastener and the target tape from each other. With a consequence, the tape fastener and the target tape may often be unintentionally disengaged from each other.

SUMMARY OF THE INVENTION

In view of the problem as has been described above, it is an object of the present invention to provide a disposable diaper improved so that a free portion of each tape fastener is reliably prevented from being disengaged from a target tape even an outer surface of the tape fastener and an inner surface of an underwear rub together during use of the diaper.

The object set forth above is achieved, according to the present invention, by a disposable diaper defining, in a longitudinal direction, front and rear waist regions and a crotch region extending between the front and rear waist regions wherein a pair of tape fasteners used to connect the front and rear waist regions with each other are attached to a pair of side flaps in the rear waist region, respectively, and the tape fasteners respectively have fixed portions permanently attached to the side flaps in the rear waist region and free portions extending outward from the fixed portions in the transverse direction and adapted to be releasably anchored on an outer side of the front waist region by means of fastening means formed on inner surfaces of the free portions.

The diaper according to the present invention further comprises the following features: Each of the tape fasteners comprises a first fibrous nonwoven fabric made of a plurality of thermoplastic synthetic resin fibers entangled one with another and thermoplastic synthetic resin coated on a generally whole area of an outer surface of the first fibrous nonwoven fabric so that the thermoplastic synthetic resin forms a substantially smooth first synthetic resin layer on an outer surface of the tape fastener.

According to one preferred embodiment of the invention, a kinetic friction coefficient of the tape fastener on its outer surface is 0.4 or less.

According to another preferred embodiment of the invention, at least one of polyethylene-, polypropylene-, polyamide-, polyester-, polyvinyl chloride- and polystyrene-based synthetic resins is used as material for the synthetic resin fiber forming the first fibrous nonwoven fabric and the first synthetic resin layer and one of the synthetic resin fiber and the first synthetic resin layer contains 25% or higher by weight of the same synthetic resin as the synthetic resin used for the other.

According to still another preferred embodiment of the invention, the side flaps of the rear waist region respective comprise a second fibrous nonwoven fabric made of a plurality of thermoplastic synthetic resin fibers entangled one with another and thermoplastic synthetic resin coated on a generally whole area of the outer surface of the second fibrous nonwoven fabric so that the thermoplastic synthetic resin forms a substantially smooth second synthetic resin layer on outer surfaces of the respective side flaps in the rear waist region.

According to further another preferred embodiment of the invention, a kinetic friction coefficient of the respective side flaps in the rear waist region is 0.4 or less.

According to an additional preferred embodiment of the invention, at least one of polyethylene-, polypropylene-, polyamide-, polyester-, polyvinyl chloride- and polystyrene-based synthetic resins is used as material for the synthetic resin fiber forming the second fibrous nonwoven fabric and the second synthetic resin layer and one of the synthetic resin fiber and the second synthetic resin layer contains 25% or higher by weight of the same synthetic resin as the synthetic resin used for the other.

According to further additional preferred embodiment of the invention, the fixed portions of the tape fasteners are permanently bonded to the side flaps in the rear waist region by means of adhesive coated on the first synthetic resin layer.

DETAILED DESCRIPTION OF THE PREFERRED EMBODIMENTS

Details of a disposable diaper according to the present invention will be more fully understood from the description given hereunder with reference to the accompanying drawings.

Figure 1:
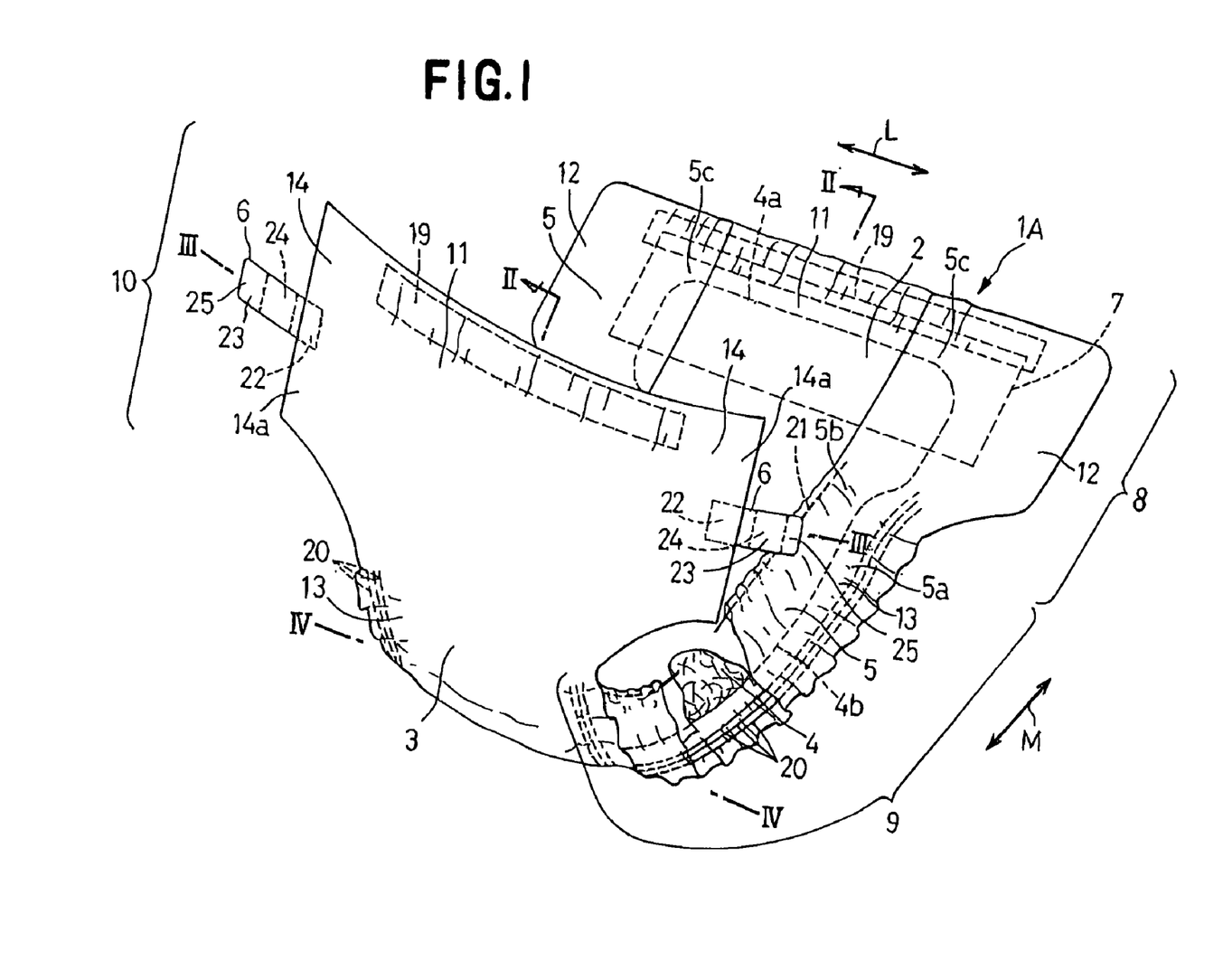
FIG. 1 is a partially cutaway perspective view showing an embodiment of the diaper.
Figure 2:
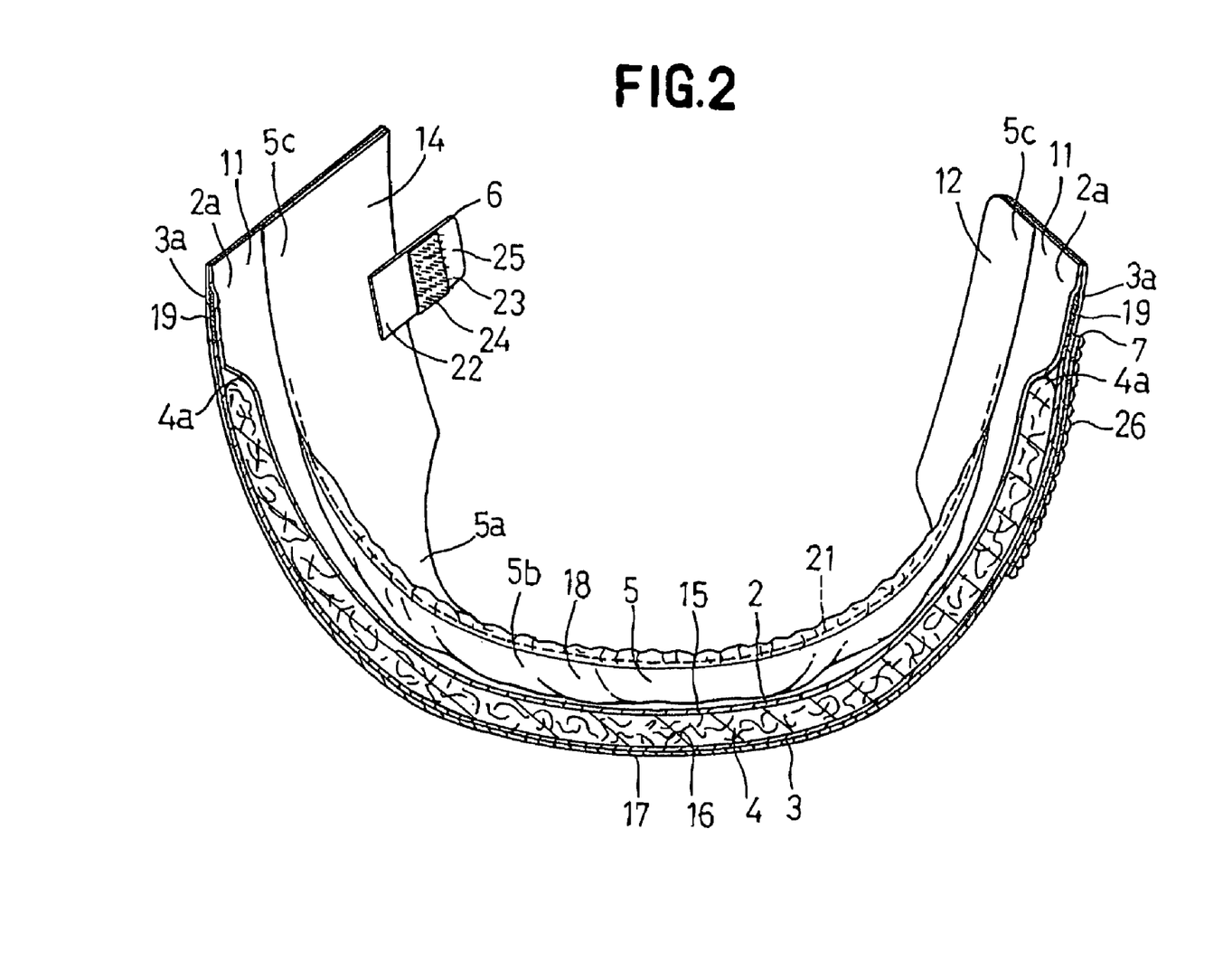
FIG. 2 is a sectional view taken along the line II—II in FIG. 1.
Figure 3:
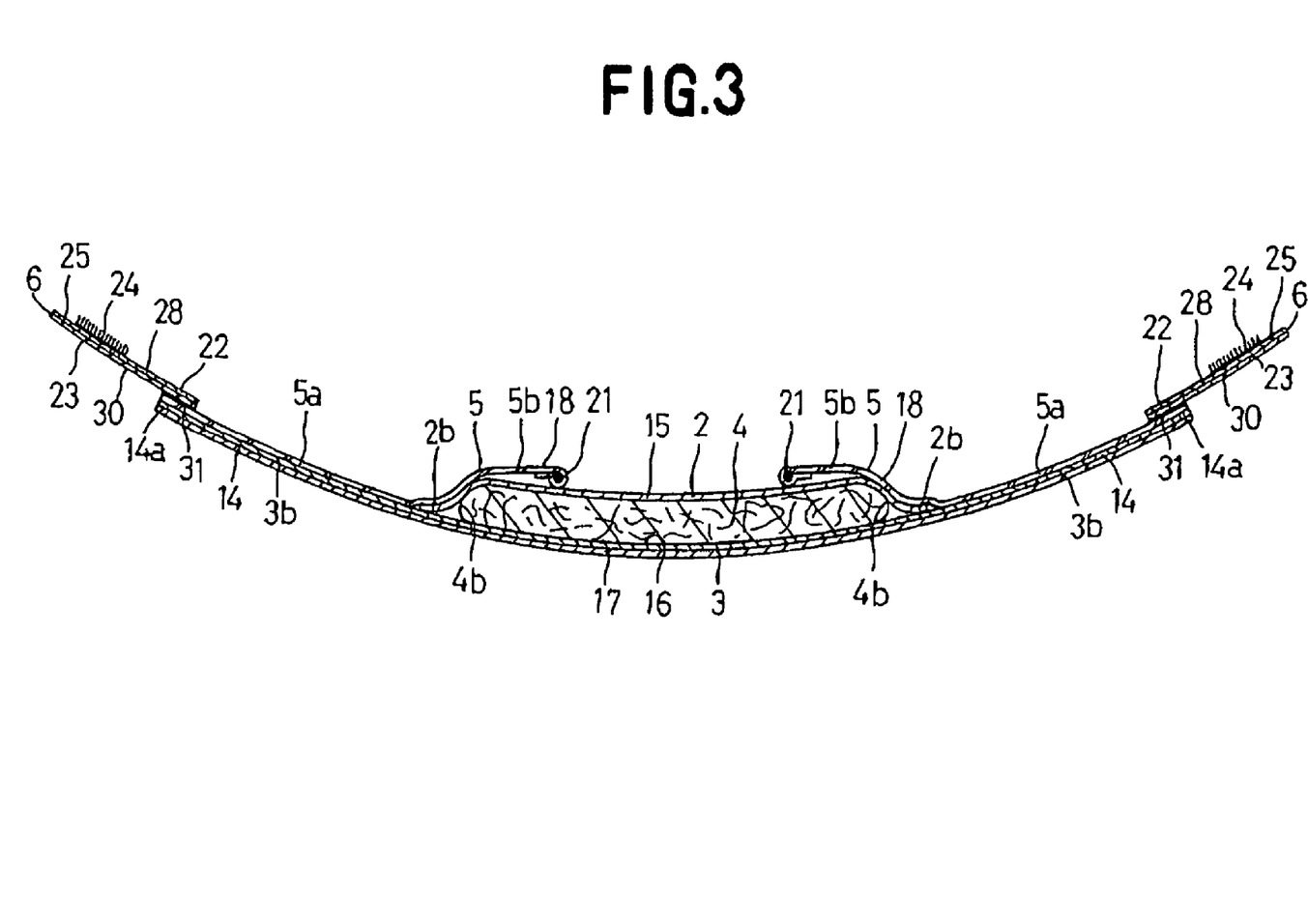
FIG. 3 is a sectional view taken along the line III—III in FIG. 1.
Figure 4:
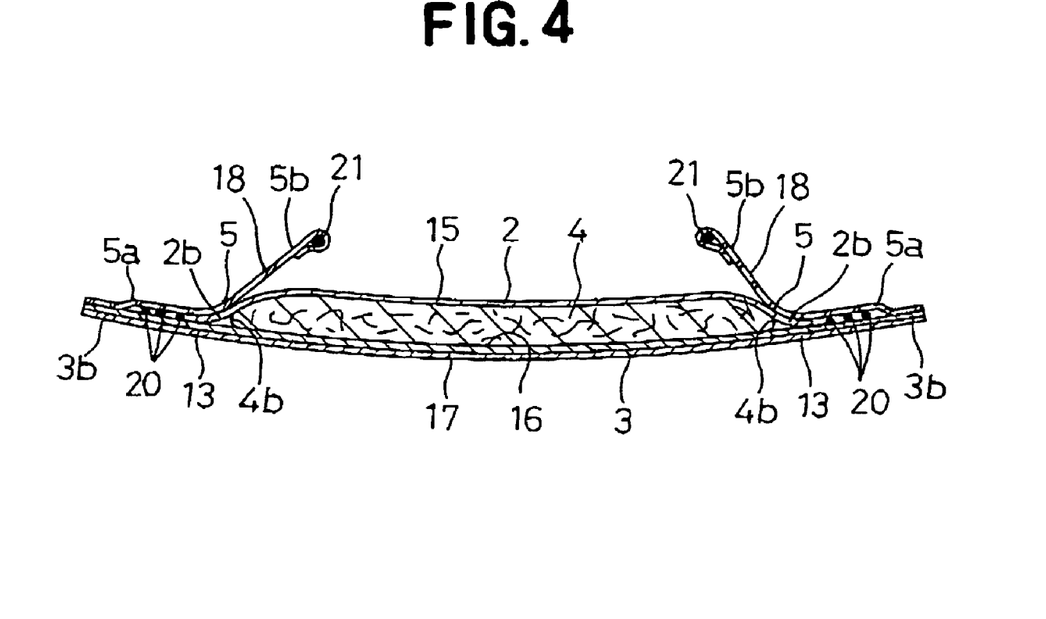
FIG. 4 is a sectional view taken along the line IV—IV in FIG. 1.

FIG. 1 is a partially cutaway perspective view showing a diaper 1A according to an embodiment of the invention, FIG. 2 is a sectional view taken along the line II—II in FIG. 1, FIG. 3 is a sectional view taken along the line III—III in FIG. 1 and FIG. 4 is a sectional view taken along the line IV—IV in FIG. 1. In FIG. 1, a transverse direction is indicated by an arrow L and a longitudinal direction is indicated by an arrow M. As used herein, "inner surfaces" of top- and backsheets 2, 3, leak-barrier sheets 5, tape fasteners 6, a target tape 7 and fibrous nonwoven fabric 28 refer to the surfaces thereof facing the wearer's skin and "outer surfaces" thereof refer to the surfaces thereof facing away from the wearer's skin.

The diaper 1A primarily comprises the liquid-pervious topsheet 2 facing the wearer's skin, the liquid-impervious backsheet 3 facing away from the wearer's skin, a liquid-absorbent core 4 interposed between these top- and backsheets 2, 3, and a pair of the leak-barrier sheets 5. In addition to these component members, the diaper 1A has a pair of the flexible tape fasteners 6 and the flexible target tape 7 which is relatively long in the transverse direction.

The diaper 1A defines, in the longitudinal direction, front and rear waist regions 8, 10, crotch region 9 extending between these waist regions 8, 10, a pair of end flaps 11 ending in the transverse direction outside longitudinally opposite ends 4a of the core 4, respectively, and paired side flaps 12, 13, 14 respectively extending in the longitudinal direction outside transversely opposite side edges 4b of the core 4. The paired side flap 12 in the front waist region 8 as well as paired side flap 14 in the rear waist regions 10 has a length dimension as measured in the transverse direction which is larger than that of the paired side flap 13 in the crotch region 9, so the diaper 1A presents a substantially hourglass-like planar shape.

The topsheet 2 is formed from a hydrophilic fibrous nonwoven fabric 15. The backsheet 3 is formed from a breathable liquid-impervious plastic film 16 and a hydrophobic fibrous nonwoven fabric 17 placed upon each other. Of the backsheet 3, the film 16 faces the wearer's skin and the nonwoven fabric 17 faces away from the wearer's skin. The film 16 and the nonwoven fabric 17 have respective surfaces opposed to each other and intermittently bonded to each other by means of adhesive (not shown). The core 4 extends between the front and rear waist regions 8, 10 and is permanently bonded to at least one of the topsheet 2 and the backsheet 3 (i e., the film 16). The leak-barrier sheets 5 are formed from a hydrophobic fibrous nonwoven fabric 18. Each of the nonwoven fabric layers 15, 17, 18 is made of a plurality of polyolefin-based thermoplastic synthetic resin crimped fibers intertwined one with another. Each of the nonwoven fabric layers 15, 17, 18 is made of a plurality of polyolefin-based thermoplastic synthetic resin fibers intertwined one with another and the film 16 is made of polyolefin-based thermoplastic synthetic resin.

Each of the end flaps 11 comprises an end portion 2a of the topsheet 2 extending outward from the associated end 4a of the core 4 in the longitudinal direction and an end portion 3a of the backsheet 3. These end portions 2a, 3a of these sheets 2, 3 are placed upon and permanently bonded to each other. Tape-like waist-surrounding elastic members 19 extending in the transverse direction are contractibly attached to the respective end flaps 11. Each of the waist-surrounding elastic members 19 is interposed between the end portion 2a of the topsheet 2 and the end portion 3a of the backsheet 3 and permanently bonded to these sheets 2, 3 while the elastic member 19 is stretched in the transverse direction at a given ratio.

The respective paired side flaps 12, 13, 14 are formed from transversely opposite side edge portions 2b, 3b of the top- and backsheets 2, 3, respectively, and fixed side edge portions 5a of the leak-barrier sheets 5 which will be described later more in details. In the respective paired side flaps 12, 13, 14, the side edge portions 2b of the topsheet 2 extend outward slightly beyond the side edges 4b of the core 4 in the transverse direction. The side edge portions 3b of the backsheet 3 as well as the fixed side edge portions 5a of the leak-barrier sheets 5 extend further outward beyond the side edge portions 2b of the topsheet 2 in the transverse direction. These side edge portions 2b, 3b, 5a of these sheets 2, 3, 5 are placed one upon another and permanently bonded one to another. Major portions of the paired side flaps 12, 14 in the front and rear waist regions 8, 10, respectively, are formed from the side edge portions 3b of the backsheet 3 and the fixed side edge portions 5a of the leak-barrier sheets 5. A plurality of strand-like leg-surrounding elastic members 20 extending in the longitudinal direction are contractibly attached to the side flaps 13 in the crotch region 9. The leg-surrounding elastic members 20 are interposed between the side edge portions 3b of the backsheet 3 and the fixed side edge portions 5a of the leak-barrier sheets 5 and are permanently bonded to these sheets 3, 5 as the elastic members 20 are stretched in the transverse direction at a given ratio.

The leak-barrier sheets 5 respectively have the fixed side edge portions 5a lying outside the respective side edges 4b of the core 4 and extending in the longitudinal direction between the front and rear waist regions 8, 10, movable portions 5b normally biased to rise above the topsheet 2 and extending in the longitudinal direction between the front and rear waist regions 8, 10 and fixed end portions 5c lying on the respective end flaps 11 and collapsed inward in the transverse direction of the diaper 1A. The movable portions 5b are provided in the vicinity of respective upper edges thereof with stretchable elastic members 21 extending in the longitudinal direction contractibly attached thereto. These elastic members 21 are wrapped with parts of the respective movable portions 5b and permanently bonded to the respective movable portions 5b. The fixed end portions 5c are permanently bonded to the inner surface of the topsheet 2 along its longitudinally opposite end portions 2a. In the leak-barrier sheets 5, the elastic members 21 contract as the diaper 1A is let curve in the longitudinal direction with the topsheet 2 inside, whereupon the movable portions 5b rise above the topsheet 2 and form barriers against bodily discharges.

The tape fasteners 6 are generally rectangular and extend outward from the side flaps 14 of the rear waist region 10 in the transverse direction. The respective tape fasteners 6 have fixed portions 22 permanently bonded to the transversely outer end portions 14a of the respective side flaps 14 and free portions 23 extending outward from the respective fixed portions 22 in the transverse direction. The free portions 23 are provided on the inner surfaces thereof with a plurality of flexible hooks 24 (fastening means) extending in a thickness direction of the diaper 1A. The free portions 23 are formed in the vicinity of distal ends thereof with finger-grips 25. These free portions 23 are releasably anchored on the outer surface of the target tape 7 through the intermediary of the hooks 24.

The target tape 7 is generally rectangular and extends on in the front waist region 8 in the transverse direction. The target tape 7 has its inner surface permanently bonded to the outer surface of the backsheet 3 (i.e., the nonwoven fabric layer 17) by means of adhesive (not shown) in intermittent or continuous manner. The target tape 7 is provided on its outer surface with a plurality of flexible loops 26 each extending in the thickness direction of the diaper 1A so as to describe a circular arc.

Figure 5:
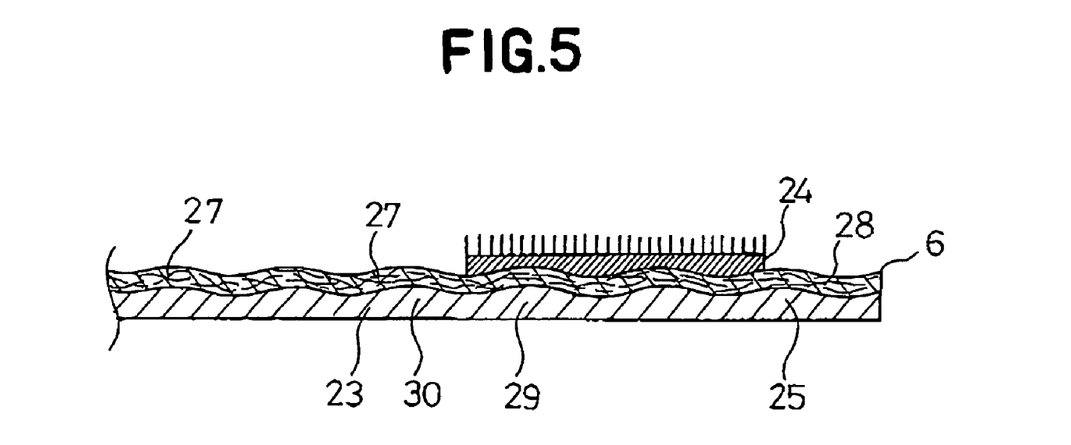
FIG. 5 is a partially scale-enlarged sectional view showing a tape fastener 6 in the sectional view of FIG. 3.
Figure 6:
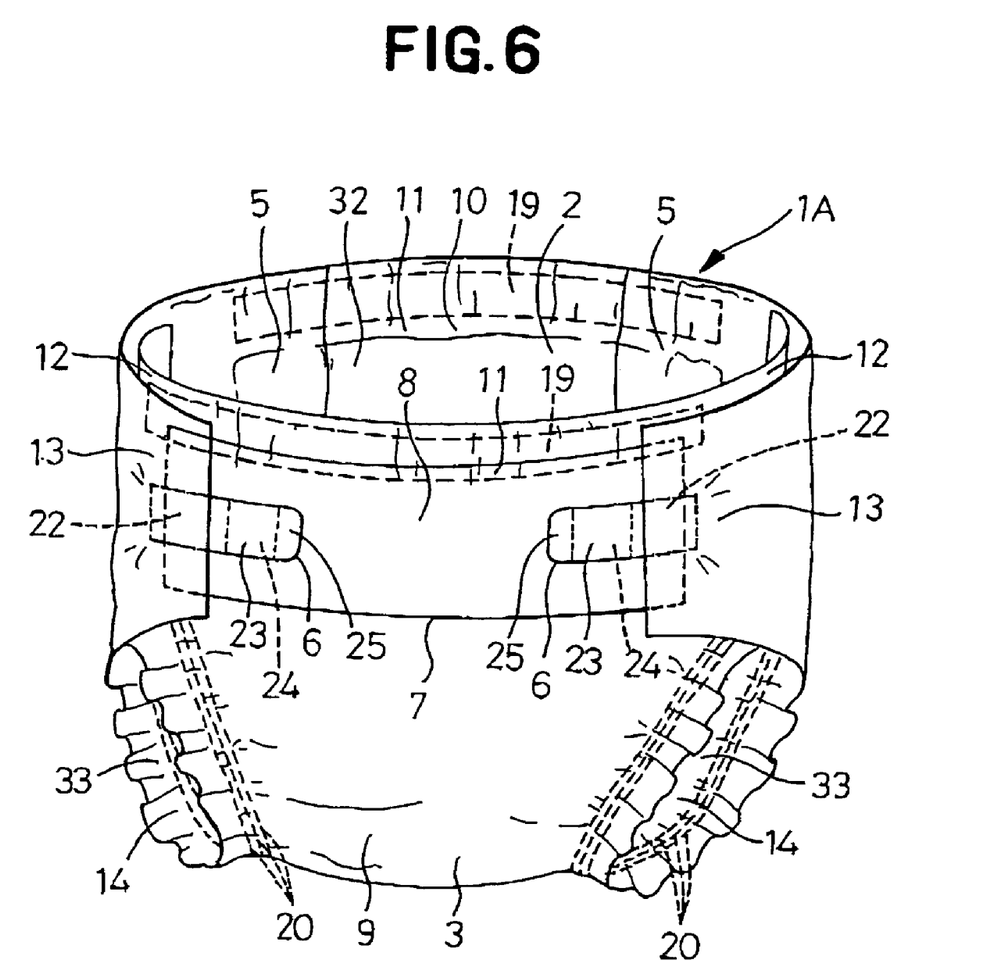
FIG. 6 is a perspective view showing the diaper as put on the wearer's body.

FIG. 5 is a partially scale-enlarged sectional view showing a tape fastener 6 in the sectional view of FIG. 3 and FIG. 6 is a perspective view showing the diaper 1A as put on the wearer's body.

The tape fastener 6 comprises a fibrous nonwoven fabric 28 (first fibrous nonwoven fabric) formed from a plurality of thermoplastic synthetic resin fibers 27 entangled one with another and thermoplastic synthetic resin 29 with which the nonwoven fabric 28 is coated over a generally whole area of its outer surface. Thermoplastic synthetic resin 29 forms a substantially smooth synthetic resin layer 30 (first synthetic resin layer) on the outer surface of the tape fastener 6. It should be understood here that the nonwoven fabric 28 may be either hydrophilic or hydrophobic.

To coat the nonwoven fabric 28 with thermoplastic synthetic resin 29, a contact coating technique (using a coater) may be utilized. In the contact coating process, a nozzle tip through which the synthetic resin 29 is discharged in molten state is placed practically in contact with the outer surface of the nonwoven fabric 28 and thereby the nonwoven fabric 28 is coated intermittently or continuously with the synthetic resin 29.

As material for the synthetic resin fiber 27 and the synthetic resin layer 30 constituting the nonwoven fabric 28, polyolefin-based thermoplastic synthetic resin may be used. As such polyolefin-based thermoplastic synthetic resin, at least one of polyethylene-, polypropylene-, polyamide-, polyester-, polyvinyl chloride- and polystyrene-based synthetic resins may be used.

It is preferred to use one and same polyolefin-based synthetic resin as material for the synthetic resin fiber 27 and the synthetic resin layer 30. For example, when polyethylene-based synthetic resin is used as material to form the synthetic resin fiber 27, it is preferred to use the same polyethylene-based synthetic resin as material to form the synthetic resin layer 30. Use of the same type of synthetic resin as material for the synthetic resin fiber 27 and the synthetic resin layer 30 is advantageous in that these two components have substantially the same melting point and a compatibility of these two components is correspondingly improved. Specifically, the synthetic resin fiber 27 and the synthetic resin 29 can be easily and reliably joined together when the outer surface of the fibrous nonwoven fabric 28 is coated with the thermoplastic synthetic resin 29.

While it is possible to use different types of polyolefin-based synthetic resin as materials for the synthetic resin fiber 27 and the synthetic resin layer 30, respectively, it is essential in this case that one of the synthetic resin fiber 27 and the synthetic resin layer 30 should contain 25% or higher by weight of the same synthetic resin as the synthetic resin used for the other. If the content of the material common to the synthetic resin fiber 27 and the synthetic resin layer 30 is less than 25% by weight, melting points of the synthetic resin fiber 27 and the synthetic resin layer 30 will be different from each other and/or compatibility between the synthetic resin fiber 27 and the synthetic resin layer 30 will be deteriorated. For example, if the melting point of the synthetic resin layer 30 is higher than the melting point of the synthetic resin fiber 27 and the compatibility between the synthetic resin fiber 27 and the synthetic resin layer 30 is insufficient, it will be impossible to join the synthetic resin layer 30 to the synthetic resin fiber 27 unless the outer surface of the nonwoven fabric 28 is coated with the thermoplastic synthetic resin 29 molten at a high temperature. In some cases, the nonwoven fabric 28 will become filmy due to the high temperature of the thermoplastic synthetic resin 29. If the nonwoven fabric 28 becomes filmy, stiffness of the tape fasteners 6 will unacceptably increase and uncomfortably irritate the wearer's skin. The synthetic resin fiber 27 preferably has a fineness in a range of 0.3 to 10 dtex. The nonwoven fabric 28 preferably has a basis weight in a range of 20 to 500 g/m$^2$, more preferably in a range of 30 to 300 g/m$^2$ and most preferably in a range of 50 to 150 g/m$^2$.

The hooks 24 attached to the tape fastener 6 are made of polyolefin-based thermoplastic synthetic resin. In the fixed portion 22 of the tape fastener 6, the synthetic resin layer 30 is coated with adhesive 31 and permanently bonded to the inner surface of the fixed side edge portion 5a of the associated leak-barrier sheet 5 (i.e., the fibrous nonwoven fabric 18) forming the side flap 14 in the rear waist region 10 by means of the adhesive 31. The target tape 7 may be formed from a fibrous nonwoven fabric made of polyolefin-based thermoplastic synthetic resin fiber or by polyolefin-based thermoplastic synthetic resin film. The loops 26 attached to the target tape 7 are made of polyolefin-based thermoplastic synthetic resin.

Parent or care personnel may put the diaper 1A on the wearer's body, for example, in a sequence as follows: Parent or care personnel may place buttock of the wearer lying face up on the developed diaper 1A, then grip the front waist region 8 and fold the crotch region 9 of the diaper 1A so that the front waist region 8 may cover the wearer's belly. Now the side flaps 14 in the rear waist region 10 may be folded inward with the tape fasteners 6 being finger gripped so that these side flaps 14 may be laid on the end flap 11 and the side flaps 12 in the front waist region 8 over the wearer's belly. Finally, the free portions 23 of the respective tape fasteners 6 may be anchored on the outer surface of the target tape 7 by means of the hooks 24.

To anchor the tape fasteners 6 on the target tape 7, the free portions 23 of the respective tape fasteners 6 may be pressed against the outer surface of the target tape 7 to put the hooks 24 and the loops 26 into mutual engagement. The diaper 1A having the front and rear waist regions 8, 10 connected with each other is formed with a waist-hole 32 and a pair of leg-holes 33. Parent or care personnel may put underwear such as pants or skirt on the wearer's body having the diaper 1A on. Movement of the wearer's body having the diaper 1A on causes the outer surfaces of the tape fasteners 6 and the inner surface of the underwear to rub together Body fluids discharged on the diaper 1A permeate the topsheet 2 and then are absorbed and retained by the core 4.

The thermoplastic synthetic resin 29 forms the synthetic resin layer 30 (i.e., first synthetic resin) on the outer surface of the respective tape fasteners 6. The synthetic resin layer 30 is sufficiently smooth to alleviate a sliding friction exerted upon the tape fasteners 6 by the underwear even when the outer surface of the tape fasteners 6 and the inner surface of the underwear rub together. In the diaper 1A, a sliding friction exerted upon the tape fasteners 6 is not so significant to cause torsion and/or turning up of the free portions 23. Significant torsion and/or turning up of the free portions 23 of the tape fasteners 6 would be exerted upon the tape fasteners 6 as well as upon the target tape 7 as a shearing force and/or a peel force intending to disengage them from one another. However, the diaper 1A is advantageously constructed so that the free portions 23 of the tape fasteners 6 are protected from such torsion and/or turning up. In this way, there is no anxiety that a torsion and/or a peel force might be exerted upon the free portions 23 of the tape fasteners 6 as well as upon the target tape 7 and cause these free portions 23 to be unintentionally disengaged from the outer surface of the target tape 7.

The adhesive 31 coated on the synthetic resin layer 30 of the fixed portions 22 is utilized to attach the fixed portions 22 of the respective tape fasteners 6 to the side flaps 14 in the rear waist region 10. The adhesive 31 spreads well on the synthetic resin layer 30 because this layer 30 is substantially smooth. Such feature ensures that, even when a substrate on which the fixed portions 22 of the respective tape fasteners 6 are to be permanently bonded is the fibrous nonwoven fabric 18 of which the outer surface is not smooth but relatively rough, these fixed portions 22 can be reliably bonded to the side flaps 14 in the rear waist region 10.

Figure 7:
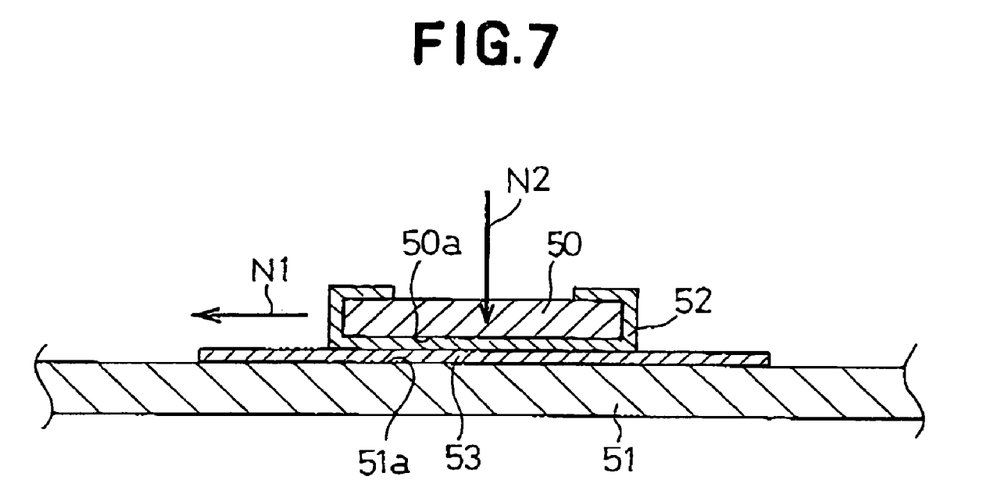
FIG. 7 is a diagram schematically illustrating how to measure a coefficient of kinetic friction.

A kinetic friction coefficient of the tape fastener 6 on its outer surface is 0.4 or less so that no significant sliding friction is exerted upon the tape fasteners 6 even when the outer surface of the tape fastener 6 and the inner surface of the underwear rub together. If the kinetic friction coefficient of the tape fastener 6 on its outer surface exceeds 0.4, unacceptably high sliding friction will be exerted upon the tape fastener 6 by the underwear and such sliding friction will cause torsion and/or turning up of the free portion 23 of the tape fastener 6. With a consequence, the free portion 23 of the tape fastener 6 and the target tape 7 engaged with each other will be subjected to a shearing force and/or a peel force. More specifically, the kinetic friction coefficient exceeding 0.4 will make it impossible to maintain the free portion 23 of the tape fastener 6 and the target tape 7 in mutual engagement and may cause the free portion 23 to be unintentionally disengaged from the target tape 7 during use of the diaper 1A. The kinetic friction coefficient of the tape fastener 6 on its outer surface was measured in accordance with JIS K 7125 by a method as will be described. FIG. 7 schematically illustrates the method for measurement of the kinetic friction coefficient.

(1) For measurement of the kinetic friction coefficient, a movable weight 50 having a smooth lower surface 50a and a fixed table 51 having a smooth upper surface 51a. Samples 52 for measurement of the kinetic friction coefficient each having a width dimension of 30 mm and a length dimension of 30 mm are made from the tape fastener 6 before attached to the diaper 1A and white cloth 53 (cotton, calico No. 3) used in a color fastness test (JIS L 0803) is prepared.

(2) The sample 52 is fixed to the lower surface 50a of the movable weight 50 using pressure sensitive adhesive double coated tape. The white cloth 53 is fixed to the upper surface 51a of the fixed table 51. The movable weight 50 has a weight of 58 g and its lower surface is subjected to a load of $6.47/cm^2$.

(3) Measurement of the kinetic friction coefficient is achieved by moving the movable weight 50 at a velocity of 10 cm/mm in a direction indicated by an arrow N1 in FIG. 7 and a kinetic friction coefficient is determined on the basis of a frictional force generated as the movable weight 50 is moved by 5 cm. Specifically, the kinetic friction coefficient is calculated from an equation: $\mu=F_D/F_P$ wherein $\mu$ represents a kinetic friction coefficient, $F_D$ represents a frictional force generated as the movable weight is moved by 5 cm and $F_P$ represents a force in a vertical direction indicated by an arrow N2 generated along a contact surface between the sample 52 for measurement and the white cloth 53.

In the diaper 1A, an engagement force at which the free portion 23 of the tape fastener 6 is engaged with the target tape 7 is preferably in a range of 0.3 to 8.0 N/(width dimension of the tape fastener). If the engagement force is less than 0.3 N/(width dimension of the tape fastener), the free portion 23 of the tape fastener 6 may sometimes be disengaged from the target tape 7 as the outer surface of the tape fastener 6 and the inner surface of the underwear rub together, even when the kinetic friction coefficient of the tape fastener 6 on its outer surface is 0.4 or less. The engagement force between the free portion 23 of the tape fastener 6 and the target tape 7 was measured by a method as follows:

(1) For measurement of the engagement force, AUTOGRAPH available from SHIMAZU Co., Ltd. (software: Trapezium Ver. 1.22 available from SHIMAZU Co., Ltd.) was used as the measuring device. In addition to this device, a fixture for peel measurement (aluminum fixture having a plane slanted at an angle of 45° with respect to a vertical axis between chucks so that a lower end of this plane can be fixed to the lower chuck of AUTOGRAPH), a pressure roller (diameter; 100 mm, width; 44 mm, weight; 700 g, hardness HS70; and reciprocating at a velocity of 5 mm/sec), a stainless plate(stainless flat plate, thickness*2 to 5 mm), a pair of gum tape strips (available from Nitto Denko Corporation, 50 mm×70 mm) and metallic clips were used.

(2) A first sample for measurement of the engagement force is made by cutting the tape fastener 6 away from the diaper 1A and a second sample for measurement of the engagement force is made by cutting a generally half of the tape fastener away from the diaper 1A, more specifically, so as to bisect the transverse dimension of the target tape 7. Then gum tape strips are coated on both surfaces of the finger-grip so that the upper chuck of AUTOGRAPH may grip the finger-grip 25 of the free portion 23 of the tape fastener6.

(3) The second sample is placed on the smooth upper surface of the stainless plate. The second sample having been smoothed is fixed to the upper surface of the stainless plate using pressure sensitive adhesive single coated tape. Now the first sample is placed on the second sample and these two samples are engaged with each other using the pressure roller (press conditions: single reciprocating at a velocity of 5 mm/min in the longitudinal direction of the first sample). A lower portion of the 135° peel measurement fixture is held by the lower chuck of AUTOGRAPH and the finger-grip 25 (including the gum tape strips) of the free portion 23 of the tape fastener 6 is held by the upper chuck. AUTOGRAPH is operated under conditions as follow: load cell=50 N; pressure range=10 N; tensile velocity=300 mm/min, and distance between the upper chuck and 135° peel measurement fixture=50 mm.

(4) the upper and lower chucks are moved away from each other in order to exert a peel force upon the first and second samples and a force generated when the first and second samples are peeled off from each other is measured. Such force generated when the first and second samples are peeled off from each other is measured ten times and an average is calculated from the results of these ten times measurements as the engagement force between the free portion 23 of the tape fastener 6 and the target tape 7.

Figure 8:
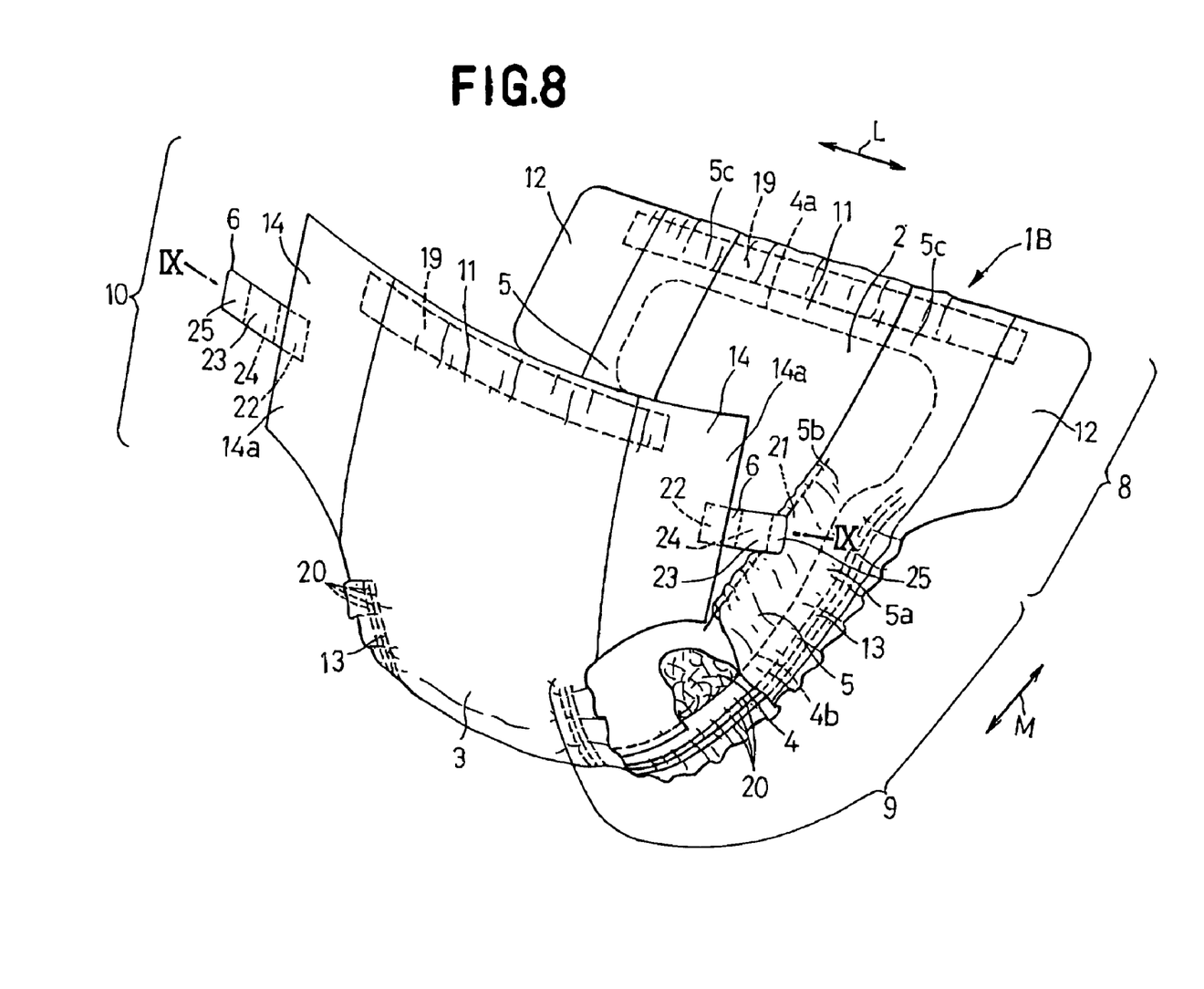
FIG. 8 is a partially cutaway perspective view showing another embodiment of the diaper.
Figure 9:
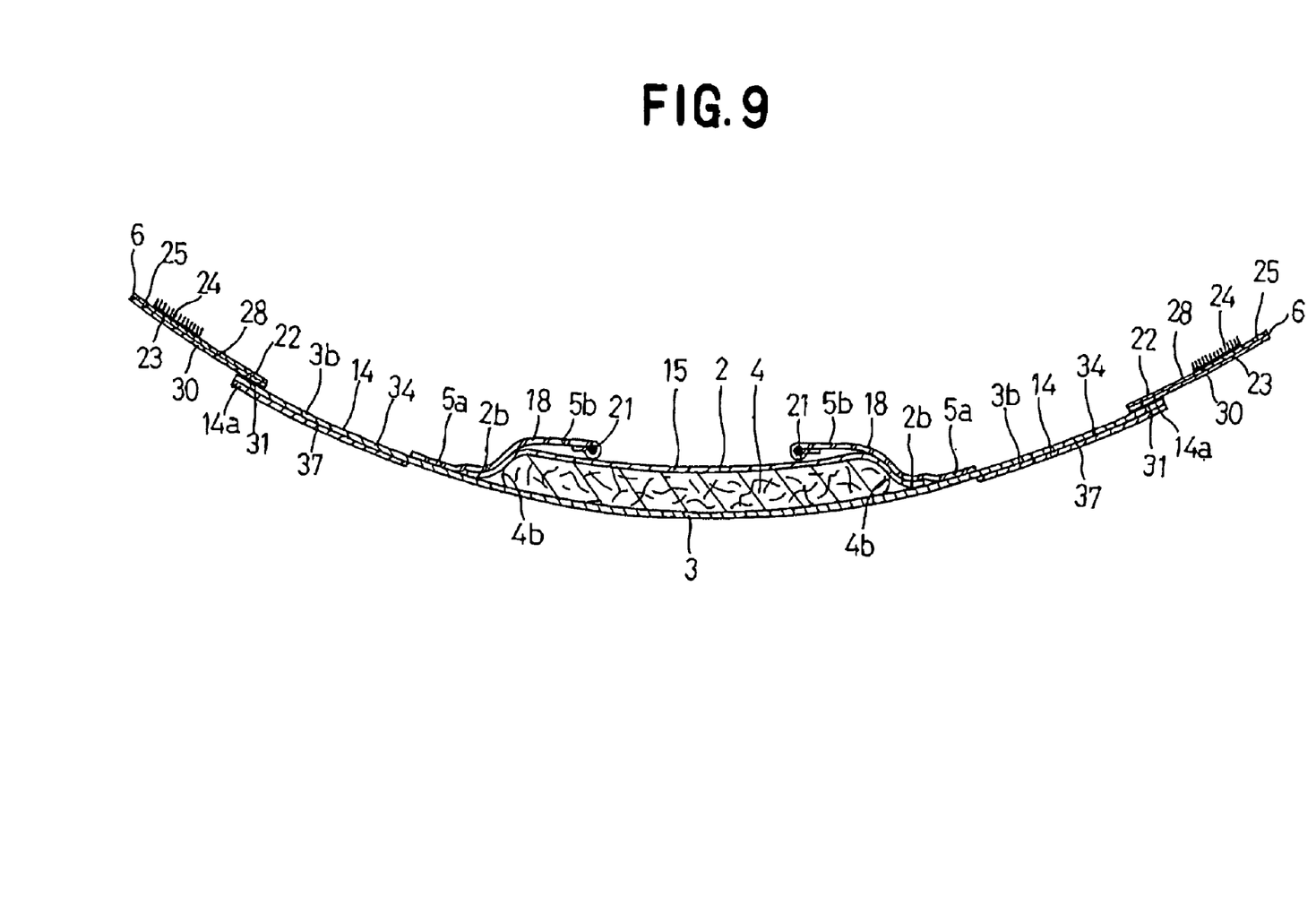
FIG. 9 is a sectional view taken along the line IX—IX in FIG. 8.
Figure 10:
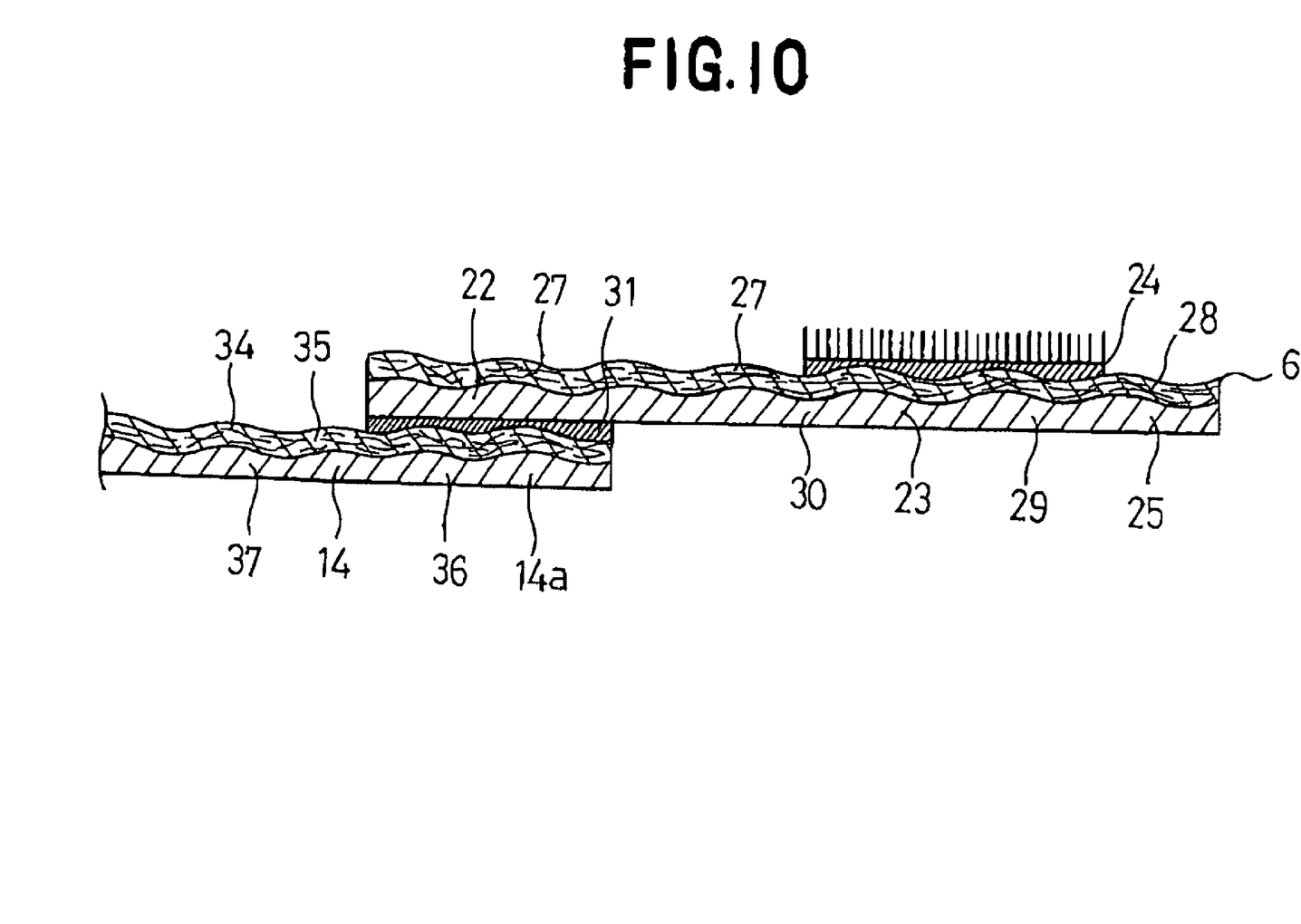
FIG. 10 is a partially scale-enlarged sectional view showing a tape fastener and a side flap in the rear waist region in the sectional view of FIG. 9.

FIG. 8 is a partially cutaway perspective view showing a diaper 1B according to another embodiment, FIG. 9 is a sectional view taken along the line IX—IX in FIG. 8 and FIG. 10 is a partially scale-enlarged sectional view showing a tape fastener 6 and a side flap 14 in the rear waist region 10 in the sectional view of FIG. 9. In FIG. 8, a transverse direction is indicated by an arrow L and a longitudinal direction is indicated by an arrow M. As used herein, "inner surface" of fibrous nonwoven fabric 34 refers to its surface facing the wearer's skin and "outer surface" of this nonwoven fabric refers to its surface facing away from the wearer's skin.

The diaper 1B primarily comprises the liquid-pervious topsheet 2 facing the wearer's skin, the liquid-impervious backsheet 3 facing away from the wearer's skin, a liquid-absorbent core 4 interposed between these top- and backsheets 2, 3, and a pair of the leak-barrier sheets 5. The diaper 1B defines, in the longitudinal direction, front and rear waist regions 8, 10, crotch region 9 extending between these waist regions 8, 10, a pair of end flaps 11 ending in the transverse direction outside longitudinally opposite ends 4a of the core 4, respectively, and paired side flaps 12, 13, 14 respectively extending in the longitudinal direction outside transversely opposite side edges 4b of the core 4. The paired side flap 12 in the front waist region 8 as well as paired side flap 14 in the rear waist regions 10 has a length dimension as measured in the transverse direction which is larger than that of the paired side flap 13 in the crotch region 9, so the diaper 1B presents a generally hourglass-like planar shape.

The topsheet 2 is formed from a hydrophilic fibrous nonwoven fabric 15 like the topsheet 2 shown by FIG. 1. The backsheet 3 is formed from a bulky hydrophobic fibrous nonwoven fabric 34 (second fibrous nonwoven fabric). The fibrous non woven fabric 34 is made of a plurality of polyolefin-based thermoplastic synthetic resin crimped fibers intertwined one with another. The core 4 is permanently bonded to at least one of the topsheet 2 and the backsheet 3. The leak-barrier sheets 5 are formed by hydrophobic fibrous nonwoven fabric 18 like them shown by FIG. 1.

Each of the end flaps 11 comprises an end portion 2a of the topsheet 2 extending outward from the associated end 4a of the core 4 in the longitudinal direction and an end portion 3a of the backsheet 3. These end portions 2a, 3a of these sheets 2, 3 are placed upon and permanently bonded to each other. Tape-like waist-surrounding elastic members 19 extending in the transverse direction are contractibly attached to the respective end flaps 11. Each of the waist-surrounding elastic members 19 is interposed between the end portion 2a of the topsheet 2 and the end portion 3a of the backsheet 3 and permanently bonded to these sheets 2, 3.

The respective paired side flaps 12, 13, 14 are formed from transversely opposite side edge portions 2b, 3b of the top- and backsheets 2, 3, respectively, and fixed side edge portions 5a of the leak-barrier sheets 5. In the respective paired side flaps 12, 14 in the front and rear waist regions 8, 10, the side edge portions 2b of the topsheet 2 and the side edge portions 5a of the leak-barrier sheets 5 extend outward slightly beyond the side edges 4b of the core 4 in the transverse direction. The side edge portions 3b of the backsheet 3 extend further outward beyond the side edge portions 2b, 5a in the transverse direction. Major portions of the paired side flaps 12, 14 are formed by the side edge portions 3b of the backsheet 3. In the side flaps 13 in the crotch region 9, the side edge portions 2b of the topsheet 2 extend outward slightly beyond the side edges 4b of the core 4 in the transverse direction and the side edge portions 3b of the backsheet 3 as well as the side edge portions 5a of the leak-barrier sheets 5 extend outward beyond the side edge portions 2b in the transverse direction. In the respective paired side flaps 12, 13, 14, the side edge portions 2b, 3b, 5a of these sheets 2, 3, 5 are placed one upon another and permanently bonded together. A plurality of strand-like leg-surrounding elastic members 20 extending in the longitudinal direction are contractibly attached to the side flaps 13 in the crotch region 9. The leg-surrounding elastic members 20 are interposed between the side edge portions 3b of the backsheet 3 and the side edge portions 5a of the leak-barrier sheets 5 and are permanently bonded to these sheets 3, 5 as the elastic members 20 are stretched in the transverse direction.

The leak-barrier sheets 5 respectively have the fixed side edge portions 5a lying outside the respective side edges 4b of the core 4 and extending in the longitudinal direction, movable portions 5b normally biased to rise above the topsheet 2 and extending in the longitudinal direction and fixed end portions 5c lying on the respective end flaps 11 and collapsed inward in the transverse direction. The fixed end portions 5c are permanently bonded to the inner surface of the topsheet 2. The movable portions 5b rise above the topsheet 2 and form barriers against bodily discharges.

The tape fasteners 6 extend outward from the side flaps 14 of the rear waist region 10 in the transverse direction. The respective tape fasteners 6 have fixed portions 22 permanently bonded to the transversely outer end portions 14a of the respective side flaps 14 and free portions 23 extending outward from the respective fixed portions 22 in the transverse direction. The free portions 23 are provided on the inner surfaces thereof with a plurality of flexible hooks 24 (fastening means) extending in a thickness direction of the diaper 1B. The free portions 23 are formed in the vicinity of distal ends thereof with finger-grips 25. These free portions 23 are releasably anchored on the outer surface of the backsheet 3 (nonwoven fabric 34) through the intermediary of the hooks 24.

The tape fastener 6 comprises fibrous nonwoven fabric 28 (first fibrous nonwoven fabric) formed by a plurality of thermoplastic synthetic resin fibers 27 entangled one with another and thermoplastic synthetic resin 29 with which the nonwoven fabric 28 is coated over a substantially whole area of its outer surface. Thermoplastic synthetic resin 29 forms a substantially smooth synthetic resin layer 30 (first synthetic resin layer) on the outer surface of the tape fastener 6. The nonwoven fabric 28 may be coated with the thermoplastic synthetic resin 29 using so-called contact coating (using a coater) technique as in the case shown by FIG. 1.

similarly to the case shown by FIG. 1, polyolefin-based thermoplastic synthetic resin may be used as material for the synthetic resin fiber 27 and the synthetic resin layer 30 constituting the nonwoven fabric 28. As such polyolefin-based thermoplastic synthetic resin, at least one of polyethylene-, polypropylene-, polyamide-, polyester-, polyvinyl chloride- and polystyrene-based synthetic resins may be used. It is preferred to use one and same polyolefin-based synthetic resin as material for the synthetic resin fiber 27 and the synthetic resin layer 30. While it is possible to use different types of polyolefin-based synthetic resin as materials for the synthetic resin fiber 27 and the synthetic resin layer 30, respectively, it is essential in this case that one of the synthetic resin fiber 27 and the synthetic resin layer 30 should contain 25% or higher by weight of the same synthetic resin as the synthetic resin used for the other. Fineness of the synthetic resin fiber 27 as well as basis weight of the nonwoven fabric 28 may be similar to those in the case shown by FIG. 1.

The hooks 24 attached to the tape fastener 6 are flexible and made of polyolefin-based thermoplastic synthetic resin. In the fixed portion 22 of the tape fastener 6, the synthetic resin layer 30 is coated with adhesive 31 and permanently bonded to the inner surface of the fixed side edge portion 3b of the backsheet 3 (i.e., the nonwoven fabric 34) forming the side flap 14 in the rear waist region 10 by means of the adhesive 31.

In the side flaps 14 of the rear waist region 10, the nonwoven fabric 34 (second fibrous nonwoven fabric) forming the backsheet 3 is coated over a generally whole area of its outer surface with thermoplastic synthetic resin 36. Thermoplastic synthetic resin 36 forms a substantially smooth synthetic resin layer 37 (second synthetic resin layer) on the outer surface of the side flaps 14 in the rear waist region 10. To coat the nonwoven fabric 34 with thermoplastic synthetic resin 36, a contact coating technique (using a coater) may be utilized like the case in which the nonwoven fabric 28 is coated with the thermoplastic synthetic resin 29.

As material for the synthetic resin fiber 35 and the synthetic resin layer 37 constituting the nonwoven fabric 34, polyolefin-based thermoplastic synthetic resin may be used. As such polyolefin-based thermoplastic synthetic resin, at least one of polyethylene-, polypropylene-, polyamide-, polyester-, polyvinyl chloride- and polystyrene-based synthetic resins may be used.

It is preferred to use one and same polyolefin-based synthetic resin as material for the synthetic resin fiber 35 and the synthetic resin layer 37. For example, when polyethylene-based synthetic resin is used as material to form the synthetic resin fiber 35, it is preferred to use the same polyethylene-based synthetic resin as material for the synthetic resin layer 35 to form the synthetic resin layer 37. Use of a same type of synthetic resin as material for the synthetic resin fiber 35 and the synthetic resin layer 37 is advantageous in that these two components have a substantially same melting point and a compatibility of these two components is correspondingly improved. Specifically, the synthetic resin fiber 35 and the synthetic resin 36 can be easily and reliably joined together when the outer surface of the fibrous nonwoven fabric 34 is coated with the thermoplastic synthetic resin 36.

While it is possible to use different types of polyolefin-based synthetic resin as materials for the synthetic resin fiber 35 and the synthetic resin layer 37, respectively, it is essential in this case that one of the synthetic resin fiber 35 and the synthetic resin layer 37 should contain 25% or higher by weight of the same synthetic resin as the synthetic resin used for the other. If the content of the material common to the synthetic resin fiber 35 and the synthetic resin layer 37 is less than 25% by weight, melting points of the synthetic resin fiber 35 and the synthetic resin layer 37 will be different from each other and/or compatibility between the synthetic resin fiber 35 and the synthetic resin layer 37 will be deteriorated. For example, if the melting point of the synthetic resin layer 37 is higher than the melting point of the synthetic resin fiber 35 and the compatibility between the synthetic resin fiber 35 and the synthetic resin layer 37 is insufficient, it will be impossible to join the synthetic resin layer 37 to the synthetic resin fiber 35 unless the outer surface of the nonwoven fabric 34 is coated with the thermoplastic synthetic resin 36 molten at a high temperature. In some cases, the nonwoven fabric 34 will become filmy due to the high temperature of the thermoplastic synthetic resin 36. If the nonwoven fabric 34 becomes filmy, stiffness of the side flaps 14 of the rear waist region 10 will unacceptably increase and uncomfortably irritate the wearer's skin.

Parent or care personnel may put the diaper 1B on the wearer's body in substantially the same sequence as in the case of FIG. 1. However, in the case of the diaper 1B, the free portions 23 of the respective tape fasteners 6 are pressed against the outer surface of the backsheet 3 to put the hooks 24 into engagement with the crimped fibers 35 forming the nonwoven fabric 34. Parent or care personnel may put underwear such as pants or skirt on the wearer's body having the diaper 1B on. Movement of the wearer's body having the diaper 1B on causes the outer surfaces of the tape fasteners 6 and the inner surface of the underwear to rub together while causing the outer surface of the side flaps 14 in the rear waist region 10 and the inner surface of the underwear to rub together The thermoplastic synthetic resin 29 forms the synthetic resin layer 30 (i.e., first synthetic resin) on the outer surface of the respective tape fasteners 6. The synthetic resin layer 30 is sufficiently smooth to alleviate a sliding friction exerted upon the tape fasteners 6 by the underwear even when the outer surface of the tape fasteners 6 and the inner surface of the underwear rub together. A sliding friction exerted upon the tape fasteners 6 is not so significant to cause torsion and/or turning up of the free portions 23. In this way, there is no anxiety that a torsion and/or a peel force might be exerted upon the free portions 23 of the tape fasteners 6 as well as upon the backsheet 3 and might cause these free portions 23 to be unintentionally disengaged from the outer surface of the backsheet (i.e., nonwoven fabric 34).

The thermoplastic synthetic resin 36 forms the substantially smooth synthetic resin layer 37 (i.e., second synthetic resin) on the outer surface of the respective side flaps 14 of the rear waist region 10. The synthetic resin layer 37 is sufficiently smooth to alleviate a sliding friction exerted upon the tape fasteners 6 by the underwear even when the outer surface of the tape fasteners 6 and the inner surface of the underwear rub together. A sliding friction exerted upon the side flaps 14 is not so significant to cause torsion and/or turning up of the side flaps 14. Significant torsion and/or turning up of the side flaps 14 would be transmitted to the tape fasteners 6 as a shearing force and/or a peel force intending to disengage the free portions of the tape fasteners 6 and the backsheet 3 from one another. However, the diaper 1B is advantageously constructed so that the side flaps 14 can be prevented from such torsion and/or turning up and the free portions 23 of the tape fasteners 6 as well as the backsheet 3 can be protected from such torsion and/or turning up. In this way, there is no anxiety that the free portions 23 might be unintentionally disengaged from the outer surface of the backsheet 3.

Similarly to the case of FIG. 1, the adhesive 31 is coated on the substantially smooth synthetic resin layer 30 of the fixed portions 22 of the tape fasteners 6 and therefore the adhesive 31 spreads well on the synthetic resin layer 30 in the diaper 1B also. Even when a substrate on which the fixed portions 22 of the respective tape fasteners 6 are to be permanently bonded is the fibrous nonwoven fabric 34 of which the outer surface is not smooth but relatively rough, these fixed portions 22 can be reliably bonded to the side flaps 14 in the rear waist region 10.

A kinetic friction coefficient of the tape fastener 6 on its outer surface is 0.4 or less. If the kinetic friction coefficient of the tape fastener 6 on its outer surface exceeds 0.4, unacceptably high sliding friction will be exerted upon the tape fastener 6 by the underwear and such sliding friction will cause torsion and/or turning up of the free portion 23 of the tape fastener 6. With a consequence, the free portion 23 of the tape fastener 6 and the backsheet 3 engaged with each other will be subjected to a shearing force and/or a peel force which may cause the free portion 23 to be unintentionally disengaged from the backsheet 3 during use of the diaper 1B.

A kinetic friction coefficient of the side flaps 14 of the rear waist region 10 on the respective outer surfaces is 0.4 or less so that no significant sliding friction is exerted upon the tape fasteners 6 even when the outer surface of the tape fastener 6 and the inner surface of the underwear rub together. If the kinetic friction coefficient of the side flaps 14 on the respective outer surfaces exceeds 0.4, unacceptably high sliding friction will be exerted upon the side flaps 14 by the underwear and such sliding friction will cause torsion and/or turning up of the side flaps 14. With a consequence, the free portion 23 of the tape fastener 6 and the backsheet 3 engaged with each other will be subjected to high shearing force and/or peel force. More specifically, the kinetic friction coefficient exceeding 0.4 will make it impossible to maintain the free portion 23 of the tape fastener 6 and the backsheet 3 in mutual engagement and may cause the free portion 23 to be unintentionally disengaged from the backsheet 3 during use of the diaper 1B.

The method for measurement of kinetic friction coefficient of the tape fastener 6 on its outer surface is same as the case of FIG. 1. The method for measurement of kinetic friction coefficient of the side flaps on the respective outer surfaces thereof is the same as the method for measurement of kinetic friction coefficient of the tape fastener 6 except that samples for measurement are prepared by cutting the side flaps 14 of the rear waist region 10 away from the diaper 1B each in a size of 30 mm width dimension×30 mm length dimension.

In the diaper 1B, an engagement force at which the free portion 23 of the tape fastener 6 is engaged with the backsheet 3 (i.e., nonwoven fabric 34) is preferably in a range of 0.3 to 8.0 N/(width dimension of the tape fastener). If the engagement force is less than 0.3 N/(width dimension of the tape fastener), the free portion 23 of the tape fastener 6 may sometimes be disengaged from the backsheet 3 as the outer surface of the tape fastener 6 and the inner surface of the underwear rub together, even when the kinetic friction coefficient of the tape fastener 6 on its outer surface is 0.4 or less. The engagement force between the free portion 23 of the tape fastener 6 and the backsheet 3 was measured by the same method as in the case of FIG. 1 except that a substantially half of the front waist region 8 is cut away from the diaper 1B, more specifically, so as to bisect the transverse dimension of the front waist region 8 to prepare second samples for measurement of engagement force.

The topsheet 2 may be formed from a hydrophobic fibrous nonwoven fabric having a plurality of apertures or plastic film having a plurality of fine apertures. The backsheet 3 and the leak-barrier sheets 5 may be formed from a composite nonwoven fabric (SM nonwoven fabric or SMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layers 15, 17, 18, 28, 34 constituting the top- and backsheets 2, 3, the leak-barrier sheets 5, the tape fasteners 6 and the target tape 7, respectively, may be selected from a group consisting of spun lace-, needle punch-, melt blown-, thermal bond-, spun bond- and chemical bond-nonwoven fabric layers. Component fibers of these nonwoven fabric layers 15, 17, 18, 28, 34 may be selected from a group consisting of core-sheath conjugate fiber, side-by-side conjugate fiber, modified macaroni fiber, microporous fiber and fused type conjugate fiber.

The core comprises a mixture of particulate or fibrous super-absorbent polymer and fluff pulp or particulate or fibrous super-absorbent polymer, fluff pulp and super-absorbent synthetic resin fiber, in any case, compressed to a desired thickness. The core 4 as a whole is preferably wrapped with a liquid-pervious sheet such as tissue paper or hydrophilic fibrous nonwoven fabric in order to prevent the core 4 from getting out of its initial shape or to prevent the polymer from falling off. The polymer may be selected from a group consisting of starch-based polymer, cellulose-based polymer and synthetic polymer.

Permanently bonding of the sheets 2, 3, 5 to one another, permanently bonding of the core 4 to the sheets 2, 3 and permanently bonding of the elastic members 19, 20, 21 to the sheets 2, 3, 5 may be achieved by use of adhesive. It is preferred to use hot melt adhesive as adhesive (including the adhesive 31). In addition to the hot melt adhesive, it is possible to use acrylic adhesive or rubber-based adhesive. The adhesive is coated on the top- and backsheets 2, 3 and the leak-barrier sheets 5 preferably in any one of spiral, wavy, zigzag, dotted or striped pattern. The top- and backsheets 2, 3 and the leak-barrier sheets 5 may be coated with the adhesive in such patterns to ensure that these sheets 2, 3, 5 are intermittently and permanently bonded one to another, the core 3 is intermittently and permanently bonded to the sheets 2, 3 and the elastic members 19, 20, 21 are intermittently and permanently bonded to the sheets 2, 3, 5.

While the free portions 23 of the respective tape fasteners 6 are provided on the respective inner surfaces thereof with the hooks 24 in both the diaper 1A and the diaper 1B, it is impossible to coat these inner surfaces of the free portions 23 with pressure-sensitive adhesive (fastening means). If the free portions 23 is coated on the respective inner surfaces thereof with the pressure-sensitive adhesive, the target tape 7 may be formed from a polyolefin-based thermoplastic synthetic resin film. In both the diaper 1A and the diaper 1B, the fixed portions 22 of the tape fasteners 6 and the side flaps 14 in the rear waist region 10 may be permanently bonded to each other using welding technique such as heat-sealing or sonic sealing technique instead of using the adhesive 31. Alternatively, in the side flaps 14 in the rear waist region 10 of the diaper 1A, the fibrous nonwoven fabric 17 (i.e., second fibrous nonwoven fabric) forming the backsheet 3 may be coated over a substantially whole area of its outer surface with the thermoplastic synthetic resin 36 to form a substantially smooth synthetic resin layer 37 (i.e., second synthetic resin layer) on the outer surfaces of the respective side flaps 14.

The disposable diaper according to the present invention is primarily characterized in that the tape fastener comprises the first fibrous nonwoven fabric and the thermoplastic synthetic resin coated on the outer surface of the first fibrous nonwoven fabric and the thermoplastic synthetic resin form the substantially smooth first synthetic resin layer on the outer surface of the tape fastener. Such unique arrangement allows the sliding friction exerted upon the tape fastener by the underwear to be alleviated even when the outer surface of the tape fastener and the inner surface of the underwear rub together. Thus the sliding friction exerted upon the tape fastener is not so sufficient to cause torsion and/or turning up of the free portion of the tape fastener. Such torsion and/or turning up of the free portion of the tape fastener can be effectively alleviated and thereby an anxiety can be eliminated that shearing force and/or peel force might be exerted upon the free portion of the tape fastener and the front waist region engaged with each other and the free portion of the tape fastener might be unintentionally disengaged from the front waist region.

In the case of the diaper constructed so that the side flaps of the rear waist region respective comprise the second fibrous nonwoven fabric and the thermoplastic synthetic resin coated on the outer surface of the second fibrous nonwoven fabric, the sliding friction exerted upon the side flaps by the underwear can be effectively alleviated even when the outer surfaces of the respective side flaps and the inner surface of the underwear rub together. This for the reason that the thermoplastic synthetic resin forms the substantially smooth second synthetic resin layer on the outer surfaces of the respective side flaps in the rear waist region In this diaper, the sliding friction exerted upon the side flaps is not so significant to cause torsion and/or turning up of the side flaps. It is possible for this diaper also to prevent the side flaps from torsion and/or turning up and thereby to protect the free portion of the tape fastener and the front waist region from shearing force and/an peel force. In this way, it is not apprehended that the free portion of the tape fastener might be unintentionally disengaged from the front waist region.

In the case of the diaper constructed so that the first synthetic resin layers constituting the fixed potions of the respective tape fasteners and the side flaps of the rear waist region are permanently bonded together by means of the adhesive, the adhesive spreads well on the tape fasteners because the adhesive is coated on the substantially smooth first synthetic resin layer. Such feature ensures that, even when a substrate on which the fixed portions of the respective tape fasteners are to be permanently bonded is the fibrous nonwoven fabric of which the outer surface is not smooth but relatively rough, these fixed portions can be reliably bonded to the side flaps in the rear waist region.

What is claimed is:

1. A disposable absorbent diaper, comprising:
   in a longitudinal direction, front and rear waist regions and a crotch region extending between said front and rear waist regions; and
   a pair of tape fasteners used to connect said front and rear waist regions with each other, said tape fasteners being attached to a pair of side flaps in said rear waist region, respectively, and respectively having fixed portions permanently attached to the side flaps in said rear waist region and free portions extending outward from said fixed portions in a transverse direction and adapted to be releasably anchored on an outer side of said front waist region by means of fastening means formed on inner surfaces of said free portions;
   each of said tape fasteners comprising;
   a first fibrous nonwoven fabric made of a plurality of thermoplastic synthetic resin fibers entangled one with another, and
   a first thermoplastic synthetic resin coating on a generally whole area of an outer surface of said first fibrous nonwoven fabric so as to form a substantially smooth first synthetic resin layer on an outer surface of said tape fastener, wherein the synthetic resin fibers which form the first fibrous nonwoven fabric and the first snthetic resin layer comprise at least one of the following materials selected from a group consisting of polyethylene, polypropylene, polyamide, polyester, polyvinyl chloride, and polystyrene-based synthetic resins; and
   a second fibrous nonwoven fabric, and a second synthetic resin layer coating on an outer surface of said second fibrous nonwoven fabric and positioned in an underlying relationship with an adhesive that bonds said first fibrous nonwoven fabric to said second fibrous nonwoven fabric.

2. The diaper according to claim 1, wherein a kinetic friction coefficient of said tape fastener on the outer surface thereof is 0.4 or less.

3. The diaper according to claim 1, wherein
   the synthetic resin fibers which form the first which form the first firous nonwoven fabric and the first synthetic resin layer comprise at least one of the following materials selected from a group consisting of polyethylene, polyethylene, polypropylene, polyamide, polyester, polyvinyl chloride, and polystyrene-based synthetic resins; and
   one of said first synthetic resin fibers and said first synthetic resin layer contains at least 25%, by weight, of the said materials.

4. The diaper according to claim 1, wherein each of the side flaps of said rear waist region comprises:
   a second fibrous nonwoven fabric made of a plurality of thermoplastic synthetic resin fibers entangled one with another, and
   thermoplastic synthetic resin coated on a substantially whole area of an outer surface of said second fibrous nonwoven fabric so as to form a substantially smooth second synthetic resin layer on outer surfaces of said side flap.

5. The diaper according to claim 4, wherein a kinetic friction coefficient of the side flaps is 0.4 or less.

6. The diaper according to claim 4, wherein
the synthetic resin fibers, which form said second fibrous nonwoven fabric, and said second synthetic resin layer comprise at least one common material selected from the group consisting of polyethylene-, polypropylene-, polyamide-, polyester-, polyvinyl chloride- and polystyrene-based synthetic resins; and
one of said synthetic resin fibers of said second fibrous nonwoven fabric and said
second synthetic resin layer contains at least 25%, by weight, of their common material.

7. The diaper according to claim 1, wherein the fixed portions of said tape fasteners are permanently bonded to die side flaps in said rear waist region by means of adhesive coated on said first synthetic resin layer.

8. A disposable absorbent diaper, comprising:
in a longitudinal direction of said diaper, front and rear waist regions and a crotch region extending between said front and rear waist regions; and
a pair of tape fasteners adapted to connect said front and rear waist regions with each other, said tape fasteners having fixed portions permanently attached to a pair of side flaps in said rear waist region and free portions extending outward from said fixed portions in a transverse direction of said diaper;
wherein each of said tape fasteners comprises
a first fibrous nonwoven fabric;
a first synthetic resin layer coated on an outer surface of said first fibrous nonwoven fabric so as to define an outer surface of said tape fastener, wherein the synthetic resin fibers which form the first fibrous nonwoven fabric and the first synthetic resin layer comprise at least one of the following materials selected from a group consisting of polyethylene, and polyropylene, polyamide, polyester, polyvinyl chloride, and polystyrene-based synthetic resins; and
a second fibrous nonwoven fabric, and a second synthetic resin layer coating on an outer surface of said second fibrous nonwonven fabric and positioned in an underlying relationship with an adhesive that bonds said first fibrous nonwoven fabric to said second fibrous nonwoven fabric, and wherein the synthetic resin fibers which form the second fibrous nonwoven fabric and the second synthetic resin layer comprise at least one of the following materials selected from a group consisting of polyethylene, polypropylene, polyamide polyester, polyvinyl chloride, and polystyrene-based synthetic resins; and
a fastening element provided on an inner surface of said tape fastener in said free portion and releasably anchorable on an outer surface of said front waist region.

9. The diaper according to claim 8, wherein a kinetic friction coefficient of said tape fastener on the outer surface thereof is 0.4 or less.

10. The diaper according to claim 8, wherein
the synthetic resin fibers which form the first fibrous nonwoven fabric and the first synthetic resin layer comprise at least one of the following materials selected from a group consisting of polyethylene, polypropylene, polyamide, polyester, polyvinyl chloride, and polystyrene-based synthetic resins; and
one of said first fibrous nonwoven fabric and said first synthetic resin layer contains at least 25%, by weight, of said materials.

11. The diaper according to claim 8, wherein a kinetic friction coefficient of the side flap on the outer surface thereof is 0.4 or less.

12. The diaper according to claim 8, wherein
the synthetic resin fibers which form the first fibrous nonwoven fabric and the first synthetic resin layer conprise at least one of the following materials selected from a group consisting of polyethylene, polypropylene, polyamide, polyester, polyvinyl chloride, and polystyrene-based synthetic resins; and
one of said second fibrous nonwoven fabric and said second synthetic resin layer contains at least 25%, by weight, of said materials.

13. The diaper according to claim 8, wherein the fixed portions of said tape fasteners are permanently bonded to the side flaps in said rear waist region by means of adhesive coated on said first synthetic resin layer.

14. The diaper according to claim 8, an outer surface of said first synthetic resin layer defines the outer surface of the tape fastener and is more planar than the outer surface of said first fibrous nonwoven fabric on which said first synthetic resin layer is coated.

15. The diaper according to claim 8, wherein
an outer surface of said second synthetic resin layer defines the outer surface of the side flap in a fixing region where the fixed portion of the respective tape fastener is permanently attached to said side flap; and
the outer surface of said second synthetic resin layer is smoother than the outer surface of said second fibrous nonwoven fabric on which said second synthetic resin layer is coated.

16. The diaper according to claim 15, wherein an outer surface of said first synthetic resin layer defines the outer surface of the tape fastener and is smoother than the outer surface of said first fibrous nonwoven fabric on which said first synthetic resin layer is coated.

17. The diaper according to claim 16, wherein the outer surface of said first synthetic resin layer in said fixing region, where an inner surface of said second fibrous nonwoven fabric is permanently bonded to the outer surface of said first synthetic resin layer of said respective tape fastener, is smoother than the inner surface of said second fibrous nonwoven fabric.

18. The diaper according to claim 17, wherein the outer surface of said first synthetic resin layer is smoother than an inner surface of said first fibrous nonwoven fabric, which defines the inner surface of the tape fastener on which said fastener element is provided.

19. The diaper according to claim 18, wherein said first synthetic resin layer is coated on the entire outer surface of said first fibrous nonwoven fabric.

20. The diaper according to claim 8, wherein an outer surface of said first synthetic resin layer defines the outer surface of the tape fastener and has a lower kinetic friction coefficient than the outer surface of said first fibrous nonwoven fabric on which said first synthetic resin layer is coated.

21. The diaper according to claim 20, wherein the outer surface of said first synthetic resin layer is non-tacky.

22. The diaper according to claim 20, wherein
the outer surface of said first synthetic resin layer is more planar than an inner surface of said first synthetic resin layer; and
the inner surface of said first synthetic resin layer is in direct physical contact with the outer surface of said first fibrous nonwoven fabric on which said first synthetic resin layer is coated.

23. The diaper according to claim 22, wherein the outer surface of said first fibrous nonwoven fabric comprising a plurality of inwardly concave regions being filled with a first synthetic resin of said first synthetic resin layer.

24. The diaper according to claim 8, wherein said second synthetic resin layer is a continuous, non-fibrous coating that fills in inwardly concave regions on the outer surface of said second fibrous nonwoven fabric.

* * * * *